US007879076B2

(12) United States Patent
Litovitz et al.

(10) Patent No.: US 7,879,076 B2
(45) Date of Patent: Feb. 1, 2011

(54) USE OF WEAK STRESSORS TO ENHANCE THE EFFECTIVENESS OF IONIZING RADIATION AND OTHER TREATMENTS OF DISEASE

(75) Inventors: Theodore Aaron Litovitz, Annapolis, MD (US); Andrea Lynn Cohen, Laurel, MD (US); Patrick Mehl, Cabin John, MD (US)

(73) Assignee: The Catholic University of America, Washington, DC (US)

( * ) Notice: Subject to any disclaimer, the term of this patent is extended or adjusted under 35 U.S.C. 154(b) by 161 days.

(21) Appl. No.: 11/510,605

(22) Filed: Aug. 28, 2006

(65) Prior Publication Data

US 2007/0184057 A1 Aug. 9, 2007

Related U.S. Application Data

(62) Division of application No. 11/346,179, filed on Feb. 3, 2006.

(51) Int. Cl.
*A61K 50/00* (2006.01)
(52) U.S. Cl. ............ 607/1; 204/157.44; 435/325; 435/173.1
(58) Field of Classification Search ............ 435/325
See application file for complete search history.

(56) References Cited

U.S. PATENT DOCUMENTS

| 5,067,952 | A | 11/1991 | Gudov et al. |
| 2001/0044643 | A1 * | 11/2001 | Litovitz ................ 607/100 |
| 2003/0195594 | A1 | 10/2003 | Litovitz |
| 2005/0214268 | A1 | 9/2005 | Cavanagh et al. |
| 2005/0288378 | A1 | 12/2005 | Yan et al. |

FOREIGN PATENT DOCUMENTS

| WO | WO 9611021 A2 * | 4/1996 |
| WO | WO 00/20022 | 4/2000 |

OTHER PUBLICATIONS

Sadekova, S et al. Induction of PBP74/mortalin/Grp75, a member of the hsp70 family, by low doses of ionizing radiation: a possible role in induced radioresistance. Int. J. Radiat. Biol. 1997. 72(6): 653-660.*
Seong, J et al. Adaptive response to ionizing radiation induced by low doses of gamma rays in human cell lines. Int. J. Radiation Oncology Biol. Phys. 1995. 33(4): 869-874.*
Prolo, P et al. Neuroendocrine-immune surveillance of osteosarcoma: emerging hypothesis. Journal of Dental Research. Jun. 2003. 82(6): 417-421.*
Grimm, RA et al. Actinomycin D in the treatmen of advanced breast cancer. Cancer Chemother. Pharmacol. 1980. 4: 195-197.*
Caney, C et al. Pre-exposure of human squamous carcinoma cells to low-doses of gamma-rays leads to an increased resistance to subsequent low-dose cisplatin treatment. Int. J. Radiat. Biol. 1999. 75(8): 963-972.*
Cohen, Bernard L. "Test of The Linear-No Threshold Theory of Radiation Carcinogenesis For Inhaled Radon Decay Products". *Health Physics*, 190, vol. 68, No. 2, pp. 157-174, Feb. 1995.
Miller, et al. "Mortality From Breast Cancer After Irradiation During Fluoroscopic Examinations in Patients Being Treated For Tuberculosis", *The New England Journal of Medicine*. vol. 321, No. 19, pp. 1285-1289, 1989.
Cardis, et al. "Effects of Low Doses and Low Dose Rates of External Ionizing Radiation: Cancer Mortality among Nuclear Industry Workers in Three Countries", *Radiation Research*. 142, pp. 117-132, 1995.
Olivieri, et al. "Adaptive Response of Human Lymphocytes to Low Concentrations of Radioactive Thymidine", *Science*. vol. 223, pp. 594-597, Feb. 10, 1984.
Wolff, Sheldon. "Aspects of the adaptive response to very low doses of radiation and other agents". *Mutation Research*. 358, pp. 135-142, 1996.
Azzam, et al. "Radiation-Induced Adaptive Response for Protection against Micronucleus Formation and Neoplastic Transformation in C3H 10T1/2 Mouse Embryo Cells", *Radiation Research*. 138, pp. S28-S31, 1994.
Azzam, et al. "Low-Dose Ionizing Radiation Decreases the Frequency of Neoplastic Transformation to a Level below the Spontaneous Rate in C3H 10T1/2 Cells". *Radiation Research*. 146, pp. 369-373, 1996.
Shadley, et al. "Characterization of the Adaptive Response to Ionizing Radiation Induced by Low Doses of X Rays to Human Lymphocytes". *Radiation Research*. 111, pp. 511-517, 1987.

(Continued)

*Primary Examiner*—Leon B. Lankford, Jr.
*Assistant Examiner*—Susan E. Fernandez
(74) *Attorney, Agent, or Firm*—Vedder Price P.C.; Ajay A. Jagtiani

(57) ABSTRACT

Enhancing the effectiveness of therapeutic ionizing radiation and other treatments of disease in which cells are to be destroyed or modified, by subjecting cells in need thereof to low-dose radiation to increase the sensitivity of the cells to subsequent subjection with a lethal dose of high dose radiation (HDR), a chemotherapeutic agent, or other type of therapeutic treatment.

5 Claims, 2 Drawing Sheets

OTHER PUBLICATIONS

Shadley, et al. "Very low doses of C-rays can cause human lymphocytes to become less susceptible to ionizing radiation". *Mutagenesis*, vol. 2, No. 2, pp. 95-96, 1987.

Shadley, et al. "Induction of the adaptive response by X-rays is dependent on radiation intensity". *Int. J. Radiat. Biol.*, vol. 56, No. 1, pp. 107-118, 1989.

Sanderson, et al. "Exposure of human lymphocytes to ionizing radiation reduces mutagenesis by subsequent ionizing radiation". *Mutation Research*. 164, pp. 347-351, 1986.

Gordon, et al. "Induction of Heat Shock Protein 70 Protects Thymocytes Against Radiation-Induced Apoptosis". *Arch. Surg*, 132(12), pp. 1277-1282, Dec. 1997.

Park, et al. "Inducible Heat-Shock Protein 70 Is Involved in the Radioadaptive Response". *Radiation Research*. 153, pp. 318-326, 2000.

Nogami, et al. "Mice chronically exposed to low does ionizing radiation possess splenocytes with elevated levels of HSP70 mRNA, HSC70 and HSP72 and with an increased capacity to proliferate". *Int. J. Radiat. Biol.* vol. 63, No. 6, pp. 775-783, 1993.

Melkonyan, et al. "Hsp70 gene expression in mouse lung cells upon chronic γ-irradiation". *Int. J. Radiat. Biol.* vol. 68, No. 3, pp. 277-280, 1995.

Sato, et al. "Low Dose X-ray Irradiation Induces Stress Proteins But Does Not Prevent Gastric Mucosal Lesion", *Physiol. Phys. Chem. & Med. NMR*. 28, pp. 103-109, 1996.

O'Rourke, et al.i *Bochemical Societ Transactions*, 20(1), p. 74S, 1991.

Lee, et al. "Role of inducible heat shock protein 70 in radiation-induced cell death". *Cell Stress & Chaperones*. 6(3), pp. 273-281, 2001.

Peper, et al. "A mathematical model of the hsp70 regulation in the cell". *Int. J. Hyperthermia*. vol. 14, No. 1, pp. 97-124, 1998.

Ibuki, et al. "Low-Dose Irradiation Induces Expression of Heat Shock Protein 70 mRNA and Thermo- and Radio-resistance in Myeloid Leukemia Cell Lime". *Biol. Phar, Bull*. vol. 21, No. 5, pp. 434-439, 1998.

International Preliminary Report on Patentability and Written Opinion of the International Search Authority for PCT/US2007/002746 mailed on Aug. 14, 2008.

Chen et al., "Enhancement of Radiation-induced Apoptosis by Preirradiation with Low-dose X-rays in Human Leukemia MOLT-4 Cells", *J. Radiat. Res.*, vol. 45, No. 2, pp. 239-243 (2004).

Supplementary European Search Report received in European Application No. 07763559.7, dated Nov. 11, 2009.

* cited by examiner

USE OF WEAK STRESSORS TO ENHANCE THE EFFECTIVENESS OF IONIZING RADIATION AND OTHER TREATMENTS OF DISEASE

CROSS-REFERENCE TO RELATED APPLICATIONS

This application is a divisional of U.S. application Ser. No. 11/346,179 filed Feb. 3, 2006. The entire disclosure and contents of the above patents and applications are hereby incorporated by reference.

BACKGROUND

1. Field of the Invention

The present invention relates generally to treating individuals with ionizing radiation and other treatments of disease.

2. Related Art

The permanent damage caused by ionizing radiation is generally believed to be directly proportional to the dose of radiation. However, an increasing body of evidence has suggested that this model is not appropriate for estimating permanent damage from low dose radiation (LDR) exposure. In fact, the growing body of evidence indicates that LDR induces protection against subsequent high dose ionizing radiation (HDR) exposure. For example, a number of epidemiology studies have shown lower cancer rates for individuals exposed to low doses of radiation (see Cohen, B. L., *Health Phys.,* 68:157-174, 1995; Miller. et al., *N. Engl. J. Med.,* 321:1285-1289, 1989; Cardis et al., *Radiat. Res.* 142: 117-132, 1995). These epidemiological results are supported by in vitro studies that show LDR exposure reduces damage from high-dose radiation (HDR) exposures (referred to in the art as radio-adaptation or hormesis).

The concept of radio-adaptation was first explored in vitro by Olivieri et al., who showed that lymphocytes that had been chronically LDR irradiated were less susceptible to chromatid aberrations from subsequent high dose x-ray exposure (see Olivieri et al., *Science,* 223:594-597 1984). This finding was confirmed for acute LDR, i.e. short term exposures low dose x-radiation, where LDR-exposed cells, following HDR exposure, showed enhanced survival and fewer chromosome breaks than controls (see Wolff, S., *Mutation Research,* 358: 135-142, 1996).

Results from other studies are consistent with these findings (see Azzam et al., *Radiat. Res.,* 138 (1 Suppl):S28-31, 1994; Azzam et al., *Radiat. Res.,* 146(4):369-73,1996; Shadley et al., *Radiation Research,* 111(3):511-517, 1987.; Shadley and Wolff, *Mutagenesis,* 2(2):95-6, 1987; Shadley and Wiencke, *Int. J. Radiat. Biol.,* 56(1):107-118, 1989; and Sanderson and Morley, *Mutat. Res.,* 164(6):347-51, 1986). As a result, it is increasingly becoming accepted that LDR exposures triggers protective cellular mechanisms that induce a radio-adaptive response (e.g. reduce the killing rate of ionizing high dose radiation). In other words, LDR exposure that triggers these protective cellular mechanisms can impede the ability to effectively treat target cells with a subsequent lethal dose of HDR. However, the inventors of the present invention have recently discovered, contrary to what is taught in the biomedical literature, that under certain conditions, LDR and other stressors may be used to increase the killing rate of HDR therapeutic exposures.

SUMMARY

According to a first broad aspect of the present invention, there is provided a method comprising the following steps: (a) providing LDR-sensitized cells of an individual; and (b) subjecting the LDR-sensitized cells to a therapeutic treatment that kills or modifies the functioning at least some of the LDR-sensitized cells.

According to a second broad aspect of the present invention, there is provided a method comprising the following steps: (a) providing sensitized cells of an individual; and (b) subjecting the sensitized cells to a therapeutic treatment that kills or modifies the functioning of at least some of the sensitized cells, wherein the level of one or more heat shock proteins in the sensitized cells are below the constitutive level of the one or more heat shock proteins for the cells.

According to a third broad aspect of the present invention, there is provided a method comprising the following steps: (a) providing maximally sensitized cells of an individual; and (b) subjecting the maximally sensitized cells to a therapeutic treatment that kills or modifies the functioning at least some of the sensitized cells.

BRIEF DESCRIPTION OF THE DRAWINGS

The invention will be described in conjunction with the accompanying drawings, in which.

DETAILED DESCRIPTION

Figure 1:
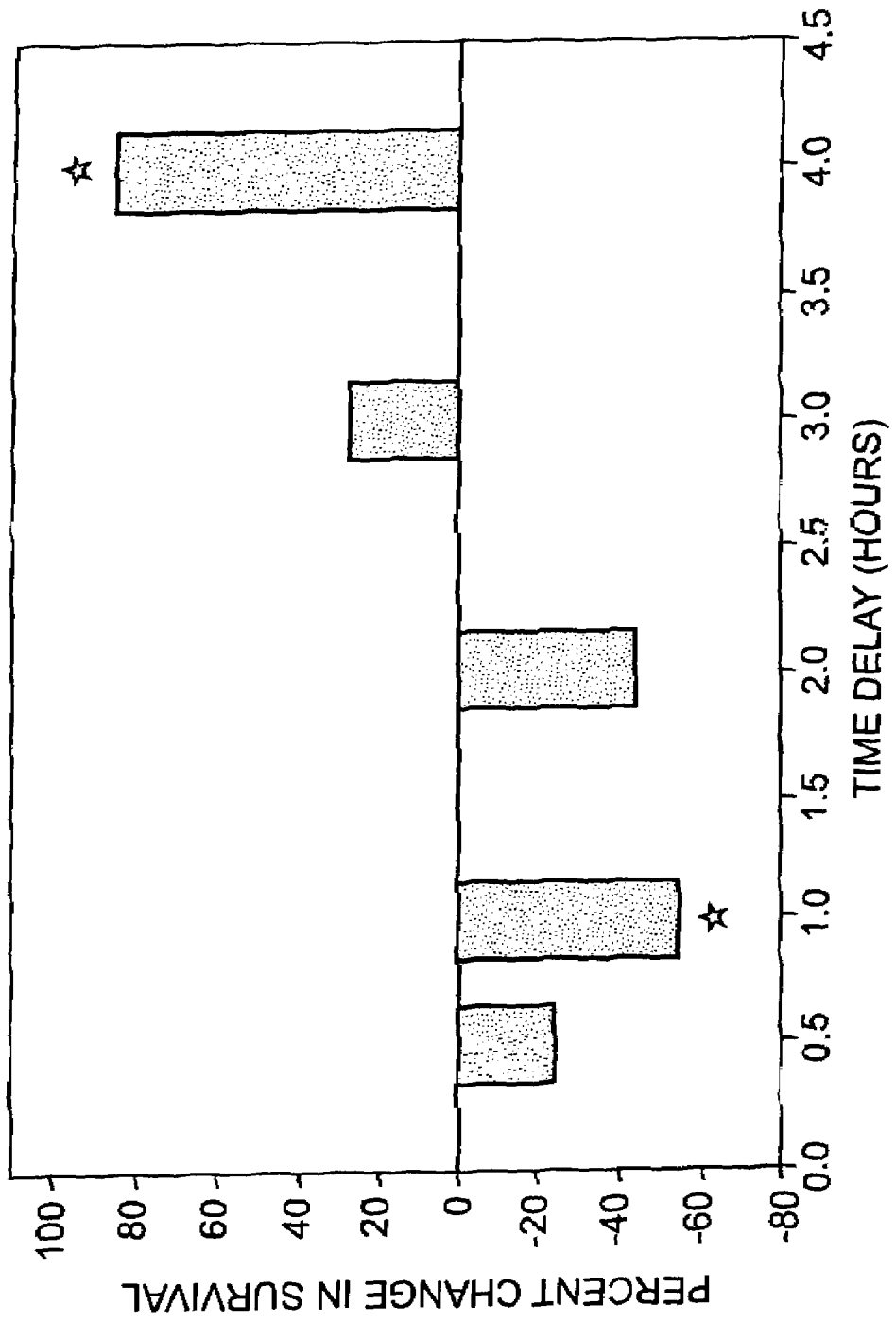
FIG. 1 is a graph depicting the effect on chick embryo survival rates following varying time delays between x-ray pre-doses of 10 cGy (LDR) and challenge doses of 15 Gy (HDR)

It is advantageous to define several terms before describing the invention. It should be appreciated that the following definitions are used throughout this application.

Definitions

For the purposes of the present invention, the term "administer" refers to any common way, orally, topically, by a focused or unfocused exposure to a radiation source, etc. For example LDR and HDR may be administered by exposure to a source of X-ray or other type of ionizing radiation. Chemotherapeutic agents may be administered by intravenous injection.

For the purposes of the present invention, the term "cancer" refers to any type of cancer including, but not limited to, skin cancer, breast cancer, bowel cancer and prostate cancer.

For the purposes of the present invention, the term "cells" refers to cells either in vivo or in vitro. Cells may be part of a tissue culture, or present in an individual or an animal, etc. Cells may also include bacteria, viruses, prions, etc.

For the purposes of the present invention, the term "chemotherapeutic agents" refers to any chemotherapeutic or cytotoxic agents including, but not limited to taxol and cisplatin.

For the purposes of the present invention, the term "chemotherapeutic treatment" or "chemotherapy" refers to treatment of an individual with a chemotherapeutic agent such as chemotherapy treatments for cancer.

For the purposes of the present invention, the term "constitutive levels" refers to the levels (concentrations) of heat shock proteins in a cell prior to a treatment with LDR or other stress in accordance with the present invention, i.e. the normal levels of heat shock proteins in the cells Until sensitized cells have recovered at least 90% of their constitutive levels of Hsps, the sensitized cells are considered substantially sensitized.

For the purposes of the present invention, the term "downregulate" the stress response is a synonym for "the inhibition of the stress response".

For the purposes of the present invention, the term "heat shock protein" or "Hsp" refers to any stress induced protective molecules that are induced by a variety of environmental stresses such as heat, ionizing and non-ionizing radiation (including electromagnetic fields and time varying magnetic fields), toxic chemicals, hypoxia (low oxygen), incorrect glucose levels, heavy metals and amino acid analogs. An important protective cellular mechanism involves activation of a stress response related to the induction of heat shock proteins (Hsps). The Hsp family comprises proteins synthesized in response to oxidative stress, which can then provide cellular protection from subsequent damage. Hsp70/72 is the most widely inducible protein in this family. For example, heat induction of Hsps in lymphocytes prior to radiation delayed apoptosis (see Gordon et al., *Arch. Surg.*, 132(12):1277-1282, 1997), and Hsp over-expression inhibited cell death following lethal x-ray exposure (see Park et al., *Radiat. Res.* 153(3): 318-326, 2000). LDR exposure has been shown to enhance Hsp levels (see Nogami et al., *Int. J. Radiat. Biol.,* 63(6): 775-783, 1993; and Melkonyan et al., Int. J. Rad. Biol., 68(3): 277-280, 1995). Sato et al. also showed that low dose X-ray irradiation induces Hsps in the gastric mucosa (see., *Physiol. Phys. Chem. & Med.* NMR, 28:103-109, 1996), and others (see O'Rourke et al., *Biochem. Soc. Trans.,* 20(1):74S, 1992) have presented evidence that LDR exposure induces Hsps in cultured myeloid leukemia and CHO cells. The entire contents and disclosures of the above documents are incorporated herein by reference.

For the purposes of the present invention, the term "high dose radiation" and "HDR" refers to any dose over 0.5 Gy or any dose that might be used therapeutically to kill cells.

For the purposes of the present invention, the term "individual" refers to a mammal such as a human being, monkey, chimpanzee, horse, dog, cat, etc.

For the purposes of the present invention, the term "ionizing radiation" refers to ionizing radiation from any source that is capable of ionizing atoms, molecules, etc. of a cell. Examples of ionizing radiation include: X-rays, ultraviolet light, gamma rays, alpha particles, beta particles, neutrons, etc. Depending on the wavelength, ultraviolet may be considered either ionizing or non-ionizing radiation.

For the purposes of the present invention, the term "LDR-sensitized" refers to cells that have been exposed to a sufficient amount of LDR for a sufficient time or dose to reduce the concentration of heat shock proteins in exposed cells by approximately 10% or more.

For the purposes of the present invention, the term "lethal dose" refers to a dose of radiation or any other therapeutic agent or modality that is capable of killing, or modifying the function of, one or more cells.

For the purposes of the present invention, the term "low dose radiation (LDR)" refers to a dose of ionizing radiation in the range of approximately 0.5 cGy to approximately 50 cGy. In one embodiment of the present invention, an LDR dose of 1 to 10 cGy may be used to LDR-sensitize cancer cells. Other dosages of LDR may be used in other embodiments of the present invention depending on the type of tissue to be treated, the disease to be treated, etc.

For the purposes of the present invention, the term "maximally sensitized" refers to cells that have been exposed to a sufficient amount of a weak stressor, such as LDR or an electromagnetic field, so that the levels for each of the heat shock proteins in the cells are less than about 10% of the constitutive levels of the respective heat shock proteins in the cells. In some embodiments, maximally sensitized cells may have a levels of heat shock proteins are each about 0% of the constitutive levels of the respective heat shock proteins in the cells.

For the purposes of the present invention, the term "modifies the functioning of a cell" refers to any alteration in the normal functioning of a cell. Examples of modifications include such modifications as: changing the proliferation rate of cells, etc.

For the purposes of the present invention, the term "sensitized" refers to cells that have been exposed to a sufficient amount of stress inducing agent to induce a stress response. Although the use of LDR to form sensitized cells is described extensively below, the present invention encompasses the use of other stress inducing agents to form sensitized cells.

For the purposes of the present invention, the term "stress inducing agent" refers to agents that induce a stress response. A stress inducing agent may be radiation-based such as LDR, non-ionizing radiation, etc. One source of non-ionizing radiation may be a laser beam. Depending on the application, ultraviolet light may be used either as LDR or as non-ionizing radiation. A stress inducing agent may also be non-radiation based such as toxic chemicals, heat, mechanical stress, etc. In one embodiment, the stress inducing agent may be electromagnetic radiation For the purposes of the present invention, the term "stress response" refers to a temporary reduction of heat shock protein by approximately 10% or more that is usually followed by an increase, above constitutive values, in the level of heat shock proteins.

For the purposes of the present invention, the term "weak stressor" refers to a stress-inducing agent that turns on the stress response of a cell, but kills either no cells or a negligible fraction of the cells exposed to the weak stressor. Examples of weak stressors include: both ionizing and non-ionizing electromagnetic radiation including: LDR, gamma-rays, X-rays, ultraviolet light, infrared radiation, laser light, microwaves, radio waves, etc.; ultrasound; time varying magnetic fields; chemical agents including various pharmaceuticals and toxic chemicals such as: chemotherapeutic agents, arsenic, etc.; increases or decreases in temperature of several degrees centigrade; mechanical stress, biological agents etc.

For the purposes of the present invention, the term "therapeutic agent" refers to any agent or procedure such as radiation, chemicals used in chemotherapy, pharmaceuticals, etc. that may be used: to modify the functioning of, to reduce the number of or to prevent the proliferation of the cells that are the target of a therapeutic treatment.

For the purposes of the present invention, the term "therapeutic treatment" refers to the administering of a therapeutic agent to an individual in a dosage or manner sufficient to reduce the number of one or more types of cells or to prevent the proliferation of one or more types of cells.

For the purposes of the present invention, the term "therapeutically effective amount" refers to an amount of a therapeutic agent capable of inhibiting the functioning or proliferation of cells and or reducing the number of living cells.

For the purposes of the present invention, the term "tumor" refers to any type of tumor including both malignant and non-malignant tumors and any abnormal proliferation of cells.

Where the definition of terms departs from the commonly used meaning of the term, applicant intends to utilize the definitions provided above, unless specifically indicated.

Description

The present invention uses low-dose radiation, and other stressors, to enhance the effectiveness of subsequent high dose ionizing radiation and other therapeutic interventions such as chemotherapy.

Radioadaptive response is the name for an observed reduced effect after exposure to a higher challenging dose (e.g. 4 Gy) when a previous priming (or preconditioning) dose (e.g. 1 cGy) was given 4 to 7 hours earlier. Hsp induction as a primary mechanism involved in radio-adaptation has been suggested. Park et al. and Lee et al. disclose studies where cell lines that did not previously exhibit a radio-adaptive response were made to over-express Hsp72 (see Park et al., *Radiat. Res.*, 153(3):318-326, 2000; and Lee et al., *Cell Stress Chaperones*, 6:273-281, 2001).

Over-expression of Hsps in the cells yielded a restoration of the radio-adaptive response. Thus many papers in the literature teach that the exposure to LDR induces a radioadaptive response (i.e. exposure to LDR makes cells less sensitive to subsequent HDR). In contrast, according to one embodiment of the present invention, conditions are provided under which LDR can make cells more sensitive to subsequent HDR.

Figure 2:
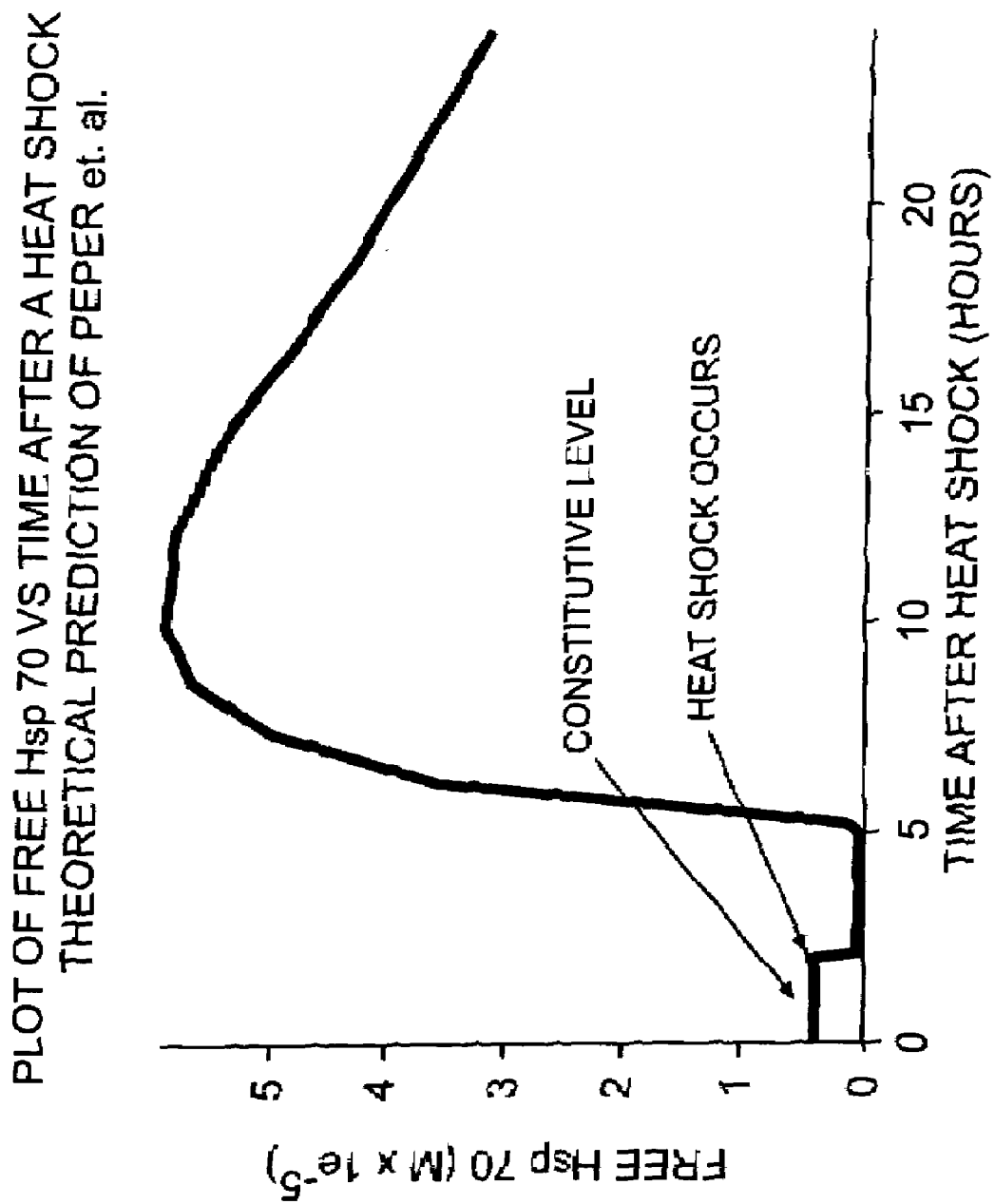
FIG. 2 is a graph depicting predicted Hsp70 levels at various times following exposure to low dose radiation (LDR) at hour 2.

When heat shock is applied, it has also been theoretically predicted (but not experimentally proven) that Hsp levels are temporarily lowered as a result. Peper et al., theoretically predict that the protection against stress might drop rapidly (i.e. within several minutes) following heat shock and that this drop lasts about 3 hours before rapidly returning to pre-conditioning levels (see Peper et al., Int. J. Hyperthermia, 14(1):97-124. 1998). FIG. 2 is a plot of Free HSP 70 vs. Time After a Heat Shock based on the theoretical prediction of Peper et. al.

Because the literature also suggests that LDR exposures induce Hsps, the inventors hypothesize that the induction of Hsp may play a role in the LDR pre-conditioning phenomenon which, the inventors have discovered, may induce de-protection against ionizing radiation In fact, the literature teaches away from our discovery by indicating that LDR exposure either has no effect or induces protection against ionizing radiation and that the induction of heat shock proteins is an important contributor to LDR-induced protection against ionizing radiation.

What has been surprisingly discovered by the inventors is that subjecting target cells (e.g., of an individual) to LDR and then waiting for times ranging from 1 minute or less to 2 hours or more, depending on the nature of the target cells, can cause those cells to be temporarily sensitized to the beneficial effects of subsequent treatment of these sensitized cells with a lethal dose of HDR or a chemotherapeutic agent. Without being bound by theory, it is believed that this sensitization of the cells subjected to LDR causes constitutive Hsp in the cells to temporarily bind Hsp to the damage sites induced by the LDR and therefore for a period of time (until new Hsp can be produced) the cell radioprotection mechanisms against HDR or other stresses are therefore reduced until the normal production of Hsps coming in about 3 hours after LDR exposure would then protect the cells against the lethal effects of subsequently subjecting the cells to a lethal dose of HDR or chemotherapeutic agent or other stress.

Because this sensitizing effect of the LDR is temporary (e.g., will dissipate over time, and typically gradually over a period of about 20 minutes to 2 hours (depending on the nature of the cell) after the cell is subjected to LDR), in one embodiment of the present invention, LDR-sensitized cells are subjected to the subsequent lethal dose of HDR, a chemotherapeutic agent or any other potentially lethal stress while these cells are still substantially LDR-sensitized. Thus, the HDR, chemotherapeutic agent or other lethal stress are preferably applied within approximately 1 minute to approximately 2 hours depending on the nature of the cells.

Depending on the cells being exposed to LDR, constitutive levels of Hsps in the cells will generally be recovered in approximately 2 to 3 hours, in some cases somewhat less than 2 hours, after the cells have been LDR-sensitized to reduce the concentration of Hsps to less than 50% of constitutive levels preferably as close to 100% reduction as possible. Therapeutic treatments may be performed, in accordance with one embodiment of the present invention, at any time from the time when the cells being treated are LDR-sensitized up until the time the cells have recovered their constitutive levels of Hsps.

The duration of the LDR used may vary depending on the intensity of the radiation, the type of cells being treated, etc. In one embodiment the treated cells may be exposed to LDR for a time of less than approximately 10 minutes.

In addition to or instead of LDR, other stress inducing agents may be used to form sensitized cells in accordance with various embodiments of the present invention. For example, a source of non-ionizing radiation, such as a laser beam emitting visible or infrared radiation, may be used to sensitize cells. Ultraviolet light may be used either as LDR or as non-ionizing radiation to produce sensitized cells. Toxic chemicals, heat, mechanical stress, etc. may also be used to produce sensitized cells in accordance with various embodiments of the present invention.

In accordance with one embodiment of the present invention, apparatuses that may be used to administer HDR to treat tumors, cancers, etc. include, for example, typical therapeutic x-ray machines or linear accelerators in use in any hospital. Other ways of administering HDR include but are not limited to gamma ray sources and ultraviolet light sources.

In order to use the apparatuses described above to therapeutically treat cells with HDR in accordance with one embodiment of the present invention, no modifications need to be made to the apparatuses or how these apparatuses are normally used other than a reduction in the usual dose.

In accordance with one embodiment of the present invention, chemotherapy treatments that may be used to treat tumors, cancers, etc. include, the intravenous injection of such chemotherapeutic agents such as: taxol, cisplatin, bleomycin, or etoposide.

In order to use the above-described chemotherapeutic treatments in accordance with one embodiment of the present invention, various modifications may need to be made to these treatments. These modifications include a reduction in dose needed for killing the tumor cells.

In accordance with one embodiment of the present invention, other therapeutic treatments that may be enhanced include, but are not limited to: antibiotic or anti-viral treatment of acute or chronic infection, or therapeutic interventions related to parasitology. In fact, any treatment of diseased tissue or cells that would be enhanced by a reduction of the stress response of the diseased tissue or cells would benefit from our discovery that weak stressors can induce a time dependent reduction in the stress response.

In order to use the above-described other therapeutic treatments in accordance with one embodiment of the present invention, a modification may need to be made to these treatments. This modification includes a reduction in dose needed to kill the tumor tissue.

EXAMPLES

Example I

Enhancing the Killing Efficacy of Ionizing Radiation

When two identical areas of cells are selected for exposure to HDR, and when one of those two areas is exposed to LDR 3 or more hours prior to the HDR exposure, then it has been observed that the survival rate of that LDR exposed area is higher than the survival rate of the cells in the unexposed area. This indicates that cells exposure first to LDR before exposure to HDR will increase the survival rate of cells exposed to HDR, thus indicating that those cells would be harder to kill after such exposure to LDR. This is an expected result, as taught by prior art.

Unexpectedly, given the same two areas of cells described in the previous paragraph, in one embodiment of the present invention, when one area of cells is first exposed to LDR to form LDR-sensitized cells and then exposed to HDR within several minutes to 2.5 hours, the survival rate of cells in that LDR exposed area of cells is lower than the survival rate of the untreated area of cells. This indicates that cells can be treated to be more sensitive (i.e. more easy to kill) to HDR and other stresses such as toxic chemicals by first exposing those cells to LDR at least 2.5 hours prior to exposure to HDR or other stresses. The preferred time window in which LDR-sensitized cells are exposed to HDR may vary by type of cells and type of tissue being treated. For example, in some types of tissue, such as cancer cells and breast cancer cells, the time window for HDR treatment may be 20 minutes to 1 hour after the cells in the tissue are sensitized with LDR.

Maximum de-protection was obtained at approximately 1½ hours after the LDR exposure. This finding of an increased sensitivity of tissues to high dose radiation immediately, i.e. within 2 hours or less, following LDR exposure has profound implications for clinical radiotherapy and chemotherapy treatments. The potential for significant improvements in cancer outcomes following radiation and chemotherapeutic treatments appears to be high.

Thus if within about several minutes to 2 hours, depending on the type of tissue one wishes to destroy, prior to an application of a therapeutic dose of x-ray energy or other types of ionizing radiation or potentially lethal stress, a low dose of radiation (i.e. LDR) is applied, the destructive effect of the therapeutic dose (e.g. HDR) is enhanced.

A low dose may be about 10 cGy but may be as low as 0.5 cGy and as high as 50 cGy. The low dose may be chosen to cause an amount of damage to the cell which can be readily repaired by the cellular Hsp or other defense mechanisms. This amount of damage may be large enough to involve (in the repair process) as much of the constitutive level of Hsp as possible so that this Hsp will not be available to protect against the HDR.

Using LDR instead of heat shock as the initial conditioning stress, the data shows that Hsp levels are reduced. This result agrees with the Peper et al. prediction heat shock reduces Hsp levels temporarily but the details in timing of the resultant reduction differ significantly from the theoretical predictions of Peper et al. (see Peper et al., *Int. J. Hyperthermia.*, 14(1): 97-124, 1998).

The inventors have found that in some cells (e.g. chick embryos) the protection decreases slowly over a period of about 1.5 hours and then over the next 1.5 hours increases back to the non-preconditioned value. Thus it is found that peak de-protection occurs about 1.5 hours after LDR exposure, see FIG. 1. The decrease in protection found in the first 1.5 hours may be related to the decrease in availability of Hsp because it is being used to repair proteins damaged by the LDR and is no longer free to protect against any HDR exposure. In the first 1.5 hours the Hsp diffuses to damaged proteins and binds with them. After 1.5 hours all the Hsp that is going to be bound is bound. The production of new Hsp starts rather soon after LDR exposure and builds up the concentration of free Hsp. This causes the decrease in the negative percent change in survival and finally causes the increase in survival after 3 hours because the new production of Hsp finally causes the Hsp levels to be greater than the normal constitutive levels of Hsp present prior to an exposure to radiation. In other cell lines, for example colorectal cancer cells and breast cancer cells, the decrease in survival can occur within one to several minutes after the LDR dose and the new production of Hsp yields Hsp levels within 20 minutes to 1 hour which are at least equal to or greater than constitutive levels and thus the survival levels become equal to or greater than that which would occur without a preconditioning LDR.

Example II

Enhancing the Killing Effect of Chemotherapeutic Agents

Focused LDR exposures may also be used in conjunction with chemotherapy where they have the advantage of being able to enhance the effect of the chemotherapeutic agent in a focused region of tissue, i.e. the tumor but not the normal tissue around it. In order to de-protect against stresses such as chemotherapeutic agents or any other lethal agent which act on the cells for hours instead of minutes, as is the case for ionizing radiation, the Hsp levels may be down-regulated for longer than 1 hour. To down-regulate the concentration of heat shock proteins for a period of more than 1 hour, LDR may be applied once a day for several days (preferably three to four days) prior to the use of chemotherapeutic agents. In this way the Hsp levels will remain down-regulated for many hours. This down regulation process may be explained as follows. When a stress is applied to a cell the level of Hsps is first decreased for about 2 hours (our invention in this application) and then after about three hours is increased. Finally after about ten hours this level returns to constitutive levels. The inventors have discovered that if one repeats this stress every day for about three days the process of adaptation to this stress occurs. Because of the adaptation process, after repeated daily stress, no Hsp are induced when the stress is applied.

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method comprising the following steps:
    (a) treating cells of an individual with a stress inducing agent for about 10 minutes or less to form sensitized cells wherein a sensitized cell is a cell wherein at least one of the heat shock proteins of the sensitized cells is reduced below its constitutive level; and
    (b) subjecting the sensitized cells to a therapeutic treatment that kills at least some of the sensitized cells, wherein step (b) is performed within about 2 hours of the sensitized cells being formed.

2. The method of claim 1, wherein step (b) is performed within about 20 minutes to about 1 hour of the sensitized cells being formed.

3. The method of claim 1, wherein step (b) is carried out before constitutive levels of heat shock proteins in the sensitized cells are recovered.

4. A method comprising the following steps:
    (a) treating cells of an individual with a stress inducing agent for about 10 minutes or less to form sensitized cells wherein a sensitized cell is a cell wherein at least one of the heat shock proteins of the sensitized cells is reduced below its constitutive level; and
    (b) subjecting the sensitized cells to a therapeutic treatment that kills at least some of the sensitized cells, wherein the therapeutic treatment kills the sensitized cells to a greater extent than unsensitized cells, wherein step (b) is performed within about 2 hours of the sensitized cells being formed.

5. The method of claim 4, wherein the survival of sensitized cells following step (b) is about 20% to about 60% reduced relative to treated unsensitized cells.

* * * * *